United States Patent [19]

Benzoni

[11] Patent Number: 4,772,592

[45] Date of Patent: * Sep. 20, 1988

[54] SKIN TREATMENT COMPOSITION

[75] Inventor: Andre J. E. Benzoni, Livry-Gargan, France

[73] Assignee: Lever Brothers Company, New York, N.Y.

[*] Notice: The portion of the term of this patent subsequent to Sep. 23, 2003 has been disclaimed.

[21] Appl. No.: 892,612

[22] Filed: Aug. 4, 1986

Related U.S. Application Data

[63] Continuation of Ser. No. 689,614, Jan. 8, 1985, Pat. No. 4,613,592.

[30] Foreign Application Priority Data

Jan. 9, 1984 [GB] United Kingdom ............... 8400482
Apr. 12, 1984 [GB] United Kingdom ............... 8409548

[51] Int. Cl.$^4$ ............................................. A61K 31/695
[52] U.S. Cl. ..................................... 514/63; 514/546; 514/859
[58] Field of Search ........................... 514/63, 859

[56] References Cited

U.S. PATENT DOCUMENTS

| | | | |
|---|---|---|---|
| 3,806,593 | 4/1974 | Swanbeck et al. | 424/28 |
| 3,984,566 | 10/1976 | Van Scott et al. | 424/283 |
| 4,054,670 | 10/1977 | Buhler | 424/168 X |
| 4,122,029 | 10/1978 | Gee et al. | 424/170 |
| 4,507,319 | 3/1985 | Barratt | 424/318 |
| 4,613,592 | 9/1986 | Benzoni | 514/63 |

FOREIGN PATENT DOCUMENTS

| | | |
|---|---|---|
| 7785 | 4/1982 | European Pat. Off. |
| 76146 | 6/1984 | European Pat. Off. |
| 1536515 | 12/1978 | United Kingdom |
| 1555796 | 11/1979 | United Kingdom |
| 2065687 | 12/1979 | United Kingdom |
| 2064363 | 6/1981 | United Kingdom |

OTHER PUBLICATIONS

"New Product Information Sheet" (Ref. No. 22-58-6-01), published by Dow Corning Europe, Aug. 1982.
"Product Information Sheet", published by Dow Corning.
"Les Copolymeres Polysiloxanes Polyethers Comme Additifs Dans Les Formulations Cosmetiques", by Dr. Kollmeier, published in Parfumes, Cosmetiques, Aromes, No. 51, Jun.-Jul. 1983, pp. 67, 68, 71, 72.

Primary Examiner—Leonard Schenkman
Attorney, Agent, or Firm—Milton L. Honig; James J. Farrell

[57] ABSTRACT

A water-in-oil emulsion suitable for topical application to human skin for the treatment of acne, comprises in addition to water a $C_1$ to $C_4$ alkyl lactate, a silicone oil ingredient containing a dispersion in a volatile siloxane of a polymer of dimethyl polysiloxane with polyoxyethylene and/or polyoxypropylene side chains having a molecular weight of from 10,000 to 50,000, a nonionic liquid emulsifier having an HLB value of from 1 to 7, and a $C_1$ to $C_4$ alkanol, the emulsion consisting essentially of an aqueous phase forming from 10 to 98% by volume and an oily phase forming from 2 to 90% by volume.

8 Claims, No Drawings

SKIN TREATMENT COMPOSITION

This is a continuation application of Ser. No. 689,614, filed Jan. 8, 1985, now U.S. Pat. No. 4,613,590.

The invention relates to a water-in-oil emulsion containing an organic lactate, particularly a water-in-oil cream containing ethyl lactate which is suited to the treatment of acne.

The primary symptom of acne is a disorder in the keratinisation of the upper part of the pilosebacous follicle. The follicular ostium becomes obstructed by hyperkeratinised and cohesive horny cells to form a microcomedone. Due to the accumulation of these hyperkeratinised cells, the follicle develops into a microcyst which may evolve as an inflammatory lesion known as a papule, or a non-inflammatory lesion known as an open comedone. The external orifice of the follicle is not visible in the microcyst, but in the open comedone, it becomes distended by a mass of darkly pigmented horny cells.

As acne develops, the follicular epithelium may break-up and cause an eruption into the dermis of keratin and sebum. The sebum contains free fatty acids derived primarily from the lytic effect of bacterial lipases (especially from *Propionibacterium acnes*) on sebum triglycerides. Inflammation due to the released free fatty acids and other bacterial by-products can ensue and a lymphocyte reaction may transform the microcyst into a papule and then into a pustule with the gathering of pus.

It is accordingly apparent that any treatment directed to inhibiting the release of these bacterial by-products of which free fatty acids from sebum triglycerides are an example, so arresting hyperkeratinisation of the follicular ostium, would effect a regression of the primary symptoms of acne and would limit the development of new acneic lesions, particularly non-inflammatory lesions (comedones).

Attempts have in the past been made to inhibit the release of these bacterial by-products by removal of the microorganisms, such as *P. acnes*, that are believed to be implicated, but these attempts have only met with limited success. The use, for example, of antibiotics can be effective in this respect, but the over liberal use of such pharmaceuticals is not to be condoned in view of their effect on gut flora and the development of antibiotic resistant strains of pathogenic microorganisms.

The topical application to acneic comedones of skin-tolerable organic acids, such as lactic acid, has also met with limited success in view of the inability of such acids to maintain a skin pH low enough to inhibit the proliferation of skin microflora for a sufficient length of time to effect regression of the disease.

It has been proposed in British Pat. No. 1 388 836 (Medisan) to treat acne with an ester of lactic acid, such as ethyl lactate, in the form of an anhydrous alcoholic solution, and in British Pat. No. 1555796 (Unilever) to treat acne with an aqueous composition containing a $C_1$ to $C_4$ alkyl lactate, and a $C_2$ to $C_4$ alkylene glycol.

A product of the type covered by this Unilever patent, and sold under the trade name "TRI-AC", is available in Great Britain as a clear liquid lotion. Although this product has been reported in the medical press as providing an effective topical treatment of the acneic condition, there has been some consumer resistance to its use owing to difficulties encountered when applying a fluid lotion of this type accurately to affected surfaces of the face, in view of its tendency to flow away from the acne lesions. Also, there exists consumer reluctance to accept that a clear liquid lotion possesses curative active ingredients. Such acne sufferers generally prefer to use an opaque cream which is easier to apply accurately to the face, in that it does not flow away from the affected area, as does a liquid lotion, and which can be seen on the skin after application, as a positive sign that the product is located topically on the acne lesion, where it will have the maximum benefit in curing the acneic condition.

Accordingly, there is a strong consumer demand for a cream containing ethyl lactate for the topical treatment of acne, and it is with the provision of such a cream that this invention is concerned.

Ethyl lactate and related $C_1$ to $C_4$ alkyl lactates are volatile polar organic liquids, and their incorporation into ordinary emulsions, such as cosmetic creams, presents a problem in that such creams are very difficult to prepare and are in any case normally unstable and not suited to commercial manufacture as syneresis rapidly occurs.

We have now discovered that stable creams can be prepared if care is taken in selecting a special volatile oil as comprising the oily phase of the emulsion.

Such emulsions have the appearance, feel and subjective characteristics of ordinary creams yet they remain stable without any signs of syneresis on storage at elevated temperatures for several months, which make them eminently suited to storage on the shop shelf before sale or storage at home before use without deterioration.

Accordingly, the invention provides a water-in-oil emulsion suitable for topical application to human skin for treating acne, which comprises, in addition to water:
(i) from 2 to 30% by weight of a $C_1$ to $C_4$ alkyl lactate, or a mixture thereof;
(ii) from 15 to 50% by weight of a silicone oil ingredient comprising a dispersion in a volatile siloxane of a polymer of dimethyl polysiloxane with polyoxyethylene and/or polyoxypropylene side chains having a molecular weight of from 10,000 to 50,000 and having the structure:

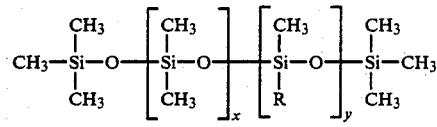

where R is

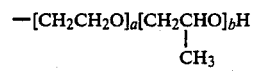

a has a value of from 9 to 115
b has a value of from 0 to 50
x has a value of from 133 to 673
y has a value of from 25 to 0.25;
(iii) from 0.5 to 10% by weight of a nonionic liquid emulsifier having an HLB value of from 1 to 7; and
(iv) from 5 to 40% by weight of a $C_1$ to $C_4$ alkanol, or a mixture thereof;
the aqueous phase forming from 10 to 98% by volume and the oily phase forming from 2 to 90% by volume of the emulsion.

The emulsion according to the invention consists of internal (discontinuous) phase which is aqueous and an external (continuous) phase which is oily. The aqueous phase will usually form from 10 to 98%, preferably from 50 to 90% by volume of the emulsion, and the oily phase will normally form from 2 to 90%, preferably from 10 to 50% by volume of the emulsion.

The emulsion according to the invention comprises a $C_1$ to $C_4$ alkyl lactate, or a mixture thereof. Examples of alkyl lactate are methyl lactate, ethyl lactate, n-propyl lactate, iso-propyl lactate, n-butyl lactate, iso-butyl lactate and tert-butyl lactate. The preferred lactate is ethyl lactate.

The effectiveness of the foregoing class of lactates in the treatment of acne is thought to be due to their ability to pass through the epidermis to reach the sebum in the sebaceous gland and pilosebaceous follicle intact, and there to dissolve in the sebum lipids where hydrolysis by lipases derived from bacterial contaminants will yield the corresponding acid and alcohol of these esters. The alcohol so formed is thought to exhibit antibacterial activity when formed in situ in the sebaceous glands and in this way the bacterial population, whose lipase activity otherwise contributes to acne formation following hydrolysis of sebum triglycerides, thus releasing free fatty acids, can thereby be reduced. Also, the lactic acid which is formed in situ is capable of reducing the pH of the environment to a value below pH 6 which will inhibit bacterial lipase activity. Free lactic acid also appears to reduce keratinisation. The net result is that release from the sebum lipids of free fatty acids (which contribute to the development of acne) is reduced, and remission of the acne condition can be observed.

The quantity of $C_1$ to $C_4$ alkyl lactate employed in the emulsion forms from 2% to 30%, preferably from 5 to 20% by weight, based on the total weight of the emulsion in which it is employed. Emulsions containing less than 2% by weight of the alkyl lactate are likely to be ineffective for treating acne; emulsions containing more than 30% by weight of the alkyl lactate are unlikely to prove more effective in the treatment of this condition than emulsions containing up to 30%. Additionally, it is possible that some skin irritation can occur when emulsions of this type containing more than 30% by weight of the alkyl lactate are applied to the skin.

The emulsion according to the invention will also comprise a silicone oil ingredient which comprises a dispersion in a volatile siloxane of a polymer of dimethyl polysiloxane with polyoxyethylene and/or polyoxypropylene side chains having a molecular weight of from 10,000 to 50,000 and having the structure:

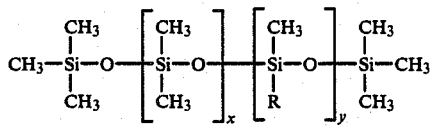

where R is

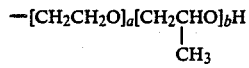

a has a value of from 9 to 115,
b has a value of from 0 to 50,
x has a value of from 133 to 673,
y has a value of from 25 to 0.25.

Preferably, the dimethyl polysiloxane polymer is one in which:
a has a value of from 10 to 114
b has a value of from 0 to 49
x has a value of from 388 to 402
y has a value of from 15 to 0.75
the group R having a molecular weight of from 1,000 to 5,000.

A particularly preferred dimethyl polysiloxane polymer is one in which:
a has the value 14
b has the value 13
x has the value 249
y has the value 1.25

The dimethyl polysiloxane polymer is usually provided as a dispersion in a volatile siloxane. The silicone oil ingredient accordingly can comprise from 1 to 20% by volume of the polymer and from 80 to 99% by volume of the volatile siloxane. Ideally, the silicone oil ingredient consists of a 10% dispersion of the polymer in the volatile siloxane.

Examples of the volatile siloxanes include volatile polydimethyl cyclosiloxane, such as one having a viscosity of less than 5 mm$^2$ sec$^{-1}$, for example DOW CORNING 344 Fluid, and volatile hexamethyldisiloxane having a viscosity of not more than 0.65 mm$^2$ sec$^{-1}$, for example DOW CORNING 200 Fluid (0.65 mm$^2$ s$^{-1}$).

A particularly preferred silicone oil ingredient is cyclomethicone and dimethicone copolyol, such as DOW CORNING Q2-3225C Formulation Aid. (DOW CORNING is a trade mark).

The emulsion can also, optionally, comprise a non-volatile silicone oil such as polydimethylsiloxane copolymer having a viscosity in excess of 5 mm$^2$ s$^{-1}$, such as that having a viscosity of from 100 to 350 mm$^2$ s$^{-1}$ for example, DOW CORNING 200 Fluid (100 mm$^2$ s$^{-1}$ or higher).

The emulsion according to the invention will normally comprise from 15 to 50%, preferably from 15 to 40% and ideally from 20 to 30% by weight of the silicone oil ingredient.

The emulsion according to the invention will also comprise an emulsifier which will normally be a nonionic liquid emulsifier having an HLB value of from 1 to 7. Preferably the emulsifier will have an HLB value of from 2 to 6.

Examples of suitable emulsifiers are:

|  | HLB Value |
|---|---|
| ARLACEL 987 (sorbitan isostearate) by Atlas | 4.3 |
| HOSTAPHAT KO 300N (moni-, di-, and tri-phosphoric esters of oleic acid) by Hoechst | 2.3 |
| IMWITOR 780K (glycerol monoisostearate) by Witco | 3.7 |
| BRIJ 92 (polyoxyethylene(2)oleyl ether) by Atlas | 4.9 |
| Triglycerol monooleate by PVO International | 4.0 |
| ARLACEL 80 (sorbitan monooleate) by Atlas | 4.3 |
| ARLACEL 83 (sorbitan sesquioleate) by Atlas | 3.7 |
| ARLACEL 85 (sorbitan trioleate) by Atlas | 1.8 |
| Decaglycerol tetraoleate by PVO International | 6.0 |
| Decaglycerol octaoleate by PVO International | 4.0 |
| AMEROX or SIMULSOL 2 (polyethoxylated(2)oleyl alcohol) by Produits Chimiques de la Montagne Noire | 6.7 |

| -continued | |
|---|---|
| | HLB Value |
| HOECHST 2721 (polyglycol sesquioleate) | 4.0 |

The quantity of emulsifier in the emulsion is from 0.5 to 10%, preferably 1 to 5% by weight of the emulsion.

If the emulsion contains less than 0.5% of emulsifier, it is unlikely that the emulsion, if obtained, will remain stable on storage, whereas if the emulsion contains more than 10% of emulsifier, the stability of the emulsion is unlikely to be further improved.

The emulsion according to the invention also comprises a $C_1$ to $C_4$ alkanol of which ethanol, n-propanol, iso-propanol and n-butanol are examples. The preferred alkanol is ethanol.

The amount of alkanol in the emulsion forms from 5 to 40%, preferably from 10 to 30% and most preferably from 15 to 30% by weight of the emulsion.

The emulsion according to the invention can also optionally comprise an electrolyte salt, whose main function can be to improve the shelf stability of the emulsion. Thus, although satisfactory emulsions can be prepared without the addition of an electrolyte, their stability under normal conditions of storage in the factory, warehouse, shop or home, which storage conditions might include temperature fluctuation of from below 0° C. to above 40° C., can be unacceptable unless at least a small quantity of electrolyte is included in the formulation.

Examples of suitable electrolyte salts include alkali metal and alkaline earth metal halides, sulphates, nitrates and carbonates or bicarbonates, in either anhydrous or hydrated form.

A particularly preferred electrolyte which can also provide a healing function, when the emulsion is applied to damaged skin, is zinc sulphate which is usually available as the heptahydrate.

The quantity of electrolyte salt employed in the emulsion forms from 0.1 to 10%, preferably from 0.2 to 5% by weight of the emulsion.

The emulsion according to the invention will also comprise water to ensure that a proper emulsion is formed and to form a solvent for water soluble ingredients of the emulsion. Usually, the emulsion will contain from 10% to 35%, preferably from 15% to 30% by weight of water based on the total weight of the emulsion. Use of emulsions containing less than 10% by weight of water are likely to leave the skin in a partly dehydrated condition. Emulsions on the other hand which contain more than 35% are likely to prove too wet for practical application to the skin, and can lead to premature hydrolysis of alkyl lactate and to product instability.

As has been stated earlier in this specification, stable emulsions containing volatile polar organic liquids such as the alkyl lactate and indeed the alkanol, both of which form essential ingredients of the emulsion, can successfully be prepared when using the special silicone oil ingredient as herein defined. These emulsions can remain stable at least for 18 months or even longer, even with fluctuating temperatures, without showing signs of syneresis.

For maximum efficacy in the topical treatment of acne, it is also important that a substantial proportion of the alkyl lactate remains unhydrolysed during storage and for this reason certain precautions can be taken. Firstly, the total amount of water employed in manufacturing the emulsion should not exceed 35% by weight in order, as stated above, to reduce to a minimum the premature hydrolysis of the alkyl lactate. Secondly, the pH of the aqueous phase during manufacture of the emulsion should be adjusted to a value of from 4 to 5.5, preferably with a buffer, although it is appreciated that it is not normally possible to determine the pH value of the emulsion once it has been prepared. Thirdly, the addition of a hydrophobic agent to the emulsion can enhance the separation of the alkyl lactate and available water in the emulsion, in order further to reduce the tendency of the alkyl lactate to hydrolyse during storage due to the proximity of water in the aqueous phase of the emulsion.

For the purpose of adjusting the pH of the aqueous phase of the emulsion during manufacture, a cosmetically acceptable agent can be employed. It is however preferred to use a buffer such as one consisting of lactic acid and triethanolamine having a pH value of from 4 to 5.5.

An example of a hydrophobic agent which can optionally be incorporated into the emulsion in order further to enhance the stability of the alkyl lactate is a hydrophobic silica having an organic moiety of from 2% to 9%, preferably from 2.5% to 8.5%. Specific examples of such hydrophobic silicas are AEROSIL R805 having an organic moiety of <9%, and AEROSIL R812 having an organic moiety of <5%, available from Degussa.

When employed, a hydrophobic agent such as AEROSIL R805 or R812 can be incorporated in the emulsion in an amount of from 0.5 to 5%, preferably from 1 to 3% by weight of the emulsion.

The emulsion according to the invention can also optionally comprise other ingredients which are generally cosmetically acceptable and which do not detract from the stability and efficacy of the emulsion. Such ingredients include emollients, solvents, humectants, thickeners, moisturisers, antioxidants, surfactants, anti-inflammatory agents, other healing agents, preservatives, buffering agents, antiseptics, antibacterial compounds, antibiotics, germicides, keratolytic agents, abradants, perfumes or skin colouring as use in face make up preparations.

The above examples of other ingredients are not intended to be exhaustive and many others can be employed. Further examples are given in McCutcheon's "Functional Materials" 1976 Annual published by M C Publishing Co., New Jersey.

Generally, the amount of each of the above other ingredients which can optionally be employed will be that recommended by the suppliers or manufacturers or that which is conventionally employed in the art, and which will not detrimentally affect the nature and function of the emulsion. Such optional ingredients can form the balance of the emulsion.

The invention also provides a process for the preparation of a water-in-oil emulsion suitable for topical application to the skin for treating acne, which process comprises the steps of forming an emulsion between a silicone oil ingredient as herein defined, a non-ionic liquid emulsifier having an HLB value of from 1 to 7, a $C_1$ to $C_4$ alkyl lactate, a $C_1$ to $C_4$ alkanol.

According to a preferred embodiment of the process of the invention, the emulsion can be prepared by employing the following process steps:

(i) an aqueous phase is prepared with water and a buffer to provide a pH of from 4 to 5.5, together with water-soluble ingredients, other than the alkyl lactate and the alkanol;
(ii) an oily phase is prepared by mixing together the silicone oil ingredient and the emulsifier;
(iii) the aqueous phase is added slowly to the oily phase with vigorous stirring at 20° C. to prepare the emulsion;
(iv) the alkyl lactate and alkanol are added with further stirring together with perfume as required; and
(v) the emulsion so obtained is filled into a container such as a lidded jar.

The emulsion according to the invention will normally take the form of an opaque cream, white in colour unless deliberately coloured by means of added colouring matter, which can be applied topically with the finger or with a suitable applicator to the affected area of skin.

Repeated application, say twice daily, to acne lesions will usually be sufficient to eliminate acne or at least cause the acneic condition to regress.

The emulsion according to the invention will normally be packaged in a suitable container such as a compressible tube or lidded jar or pot.

The invention is illustrated by the following examples:

EXAMPLE 1

An anti-acne cream was prepared from the following ingredients:

| | % |
|---|---|
| Silicone oil ingredient | |
| Silicone Q2-3225C | 29 |
| Emulsifier | |
| Polyglycol sesquioleate | 2 |
| Alkyl lactate | |
| Ethyl lactate | 11.5 |
| Alkanol | |
| Ethanol | 21 |
| Electrolyte | |
| Zinc sulphate (ZnSO$_4$.7H$_2$O) | 0.3 |
| Other ingredients | |
| Titanium dioxide | 0.5 |
| Buffer (pH 5.5) | 2.5 |
| Preservative, perfume, antioxidant | 2.5 |
| Emollient | 7 |
| Water | 23.7 |
| | 100 |

The emulsion was stable at storage temperatures up to 42° C. for up to sixteen months. It was also stable to freeze-thaw cycling.

The emulsion can be used in the topical treatment of acne.

EXAMPLE 2

An anti-acne cream was prepared from the following ingredients:

| | % |
|---|---|
| Silicone oil ingredient | |
| Silicone Q2-3225C | 24 |
| Emulsifier | |
| Polyglycol sesquioleate | 2 |
| Alkyl lactate | |
| Ethyl lactate | 11.5 |
| Alkanol | |
| Ethanol | 21 |
| Electrolyte | |
| Zinc sulphate (ZnSO$_4$.7H$_2$O) | 0.3 |
| Hydrophobic agent | |
| AEROSIL R805 | 3 |
| Other ingredients | |
| Titanium dioxide | 0.5 |
| Buffer (pH 5) | 2.5 |
| Preservative, perfume, antioxidant | 2.5 |
| Emollient | 7.2 |
| Water | 25.5 |
| | 100 |

The emulsion was stable at storage temperatures up to 42° C. for up to sixteen months. It was also stable to freeze-thaw cycling.

The emulsion can be used in the topical treatment of acne.

EXAMPLE 3

An anti-acne cream was prepared from the following ingredients:

| | % |
|---|---|
| Silicone oil ingredient | |
| Silicone Q2-3225C | 28 |
| Emulsifier | |
| Polyglycol sesquioleate | 2 |
| Alkyl lactate | |
| Ethyl lactate | 11.5 |
| Alkanol | |
| Ethanol | 21 |
| Electrolyte | |
| Zinc sulphate (ZnSO$_4$.7H$_2$O) | 0.3 |
| Hydrophobic agent | |
| AEROSIL R805 | 1 |
| Other ingredients | |
| Titanium dioxide | 0.5 |
| Buffer (pH 5.5) | 2.5 |
| Preservative, perfume, antioxidant | 2.5 |
| Emollient | 7.2 |
| Water | 23.5 |
| | 100 |

The emulsion was stable at storage temperatures up to 42° C. for up to four months. It was also stable to freeze-thaw cycling.

The emulsion can be used in the topical treatment of acne.

EXAMPLE 4

An anti-acne cream was prepared from the following ingredients:

| | % |
|---|---|
| Silicone oil ingredient | |
| Silicone Q2-3225C | 28 |
| Emulsifier | |
| Polyglycol sesquioleate | 2 |
| Alkyl lactate | |
| Ethyl lactate | 11.5 |
| Alkanol | |
| Ethanol | 28.9 |
| Electrolyte | |
| Zinc sulphate (ZnSO$_4$.7H$_2$O) | 0.3 |

| | % |
|---|---|
| Hydrophobic agent | |
| AEROSIL R805 | 2 |
| Other ingredients | |
| Titanium dioxide | 0.5 |
| Buffer (pH 5.5) | 2.5 |
| Preservative, perfume, antioxidant | 2.5 |
| Emollient | 7 |
| Water | 14.8 |
| | 100 |

The emulsion was stable at storage temperatures up to 42° C. for up to three months. It was also stable to freeze-thaw cycling.

The emulsion can be used in the topical treatment of acne.

EXAMPLE 5

An anti-acne cream can be prepared from the following ingredients:

| | % |
|---|---|
| Silicone oil ingredient | |
| Silicone Q2-3225C | 30 |
| Emulsifier | |
| Sorbitan isostearate | 2.5 |
| Alkyl lactate | |
| Methyl lactate | 10 |
| Alkanol | |
| Ethanol | 10 |
| iso-Propanol | 11 |
| Electrolyte | |
| Zinc sulphate (ZnSO$_4$.7H$_2$O) | 0.3 |
| Other ingredients | |
| Titanium dioxide | 0.5 |
| Buffer (pH 5.5) | 2.5 |
| Preservative, perfume, antioxidant | 2.5 |
| Emollient | 7.2 |
| Water | 23.5 |
| | 100 |

The emulsion will be stable at storage temperatures up to 42° C. for several months. It will also be stable to freeze-thaw cycling.

The emulsion can be used in the topical treatment of acne.

EXAMPLE 6

An anti-acne cream can be prepared from the following ingredients:

| | % |
|---|---|
| Silicone oil ingredient | |
| Silicone Q2-3225C | 25 |
| Emulsifier | |
| Glycerol monoisostearate | 3 |
| Alkyl lactate | |
| n-Propyl-lactate | 12 |
| Alkanol | |
| iso-Propanol | 18 |
| Electrolyte | |
| Zinc sulphate (ZnSO$_4$.7H$_2$O) | 0.3 |
| Other ingredients | |
| Titanium dioxide | 0.5 |
| Buffer (pH 5.5) | 2.5 |
| Preservative, perfume, antioxidant | 2.5 |
| Emollient | 6 |
| Water | 30.2 |
| | 100 |

The emulsion will be stable at storage temperatures up to 42° C. for several months. It will also be stable to freeze-thaw cycling.

The emulsion can be used in the topical treatment of acne.

EXAMPLE 7

An anti-acne cream can be prepared from the following ingredients:

| | % |
|---|---|
| Silicone oil ingredient | |
| Silicone Q2-3225C | 32 |
| Emulsifier | |
| Polyoxyethylene (2) oleylether | 3 |
| Alkyl lactate | |
| iso-Propyl lactate | 12 |
| Alkanol | |
| Ethanol | 12 |
| iso-Propanol | 12 |
| Electrolyte | |
| Zinc sulphate (ZnSO$_4$.7H$_2$O) | 0.3 |
| Other ingredients | |
| Titanium dioxide | 0.5 |
| Buffer (pH 5.5) | 2.5 |
| Preservative, perfume, antioxidant | 2.5 |
| Emollient | 8 |
| Water | 15.2 |
| | 100 |

The emulsion will be stable at storage temperatures up to 42° C. for several months. It will also be stable to freeze-thaw cycling.

The emulsion can be used in the topical treatment of acne.

EXAMPLE 8

An anti-acne cream was prepared from the following ingredients:

| | % |
|---|---|
| Silicone oil ingredient | |
| Silicone Q2-3225C | 30 |
| Emulsifier | |
| Sorbitan monoleate | 2.5 |
| Alkyl lactate | |
| n-Butyl lactate | 12 |
| Alkanol | |
| n-Propanol | 22 |
| Electrolyte | |
| Zinc sulphate (ZnSO$_4$.7H$_2$O) | 0.3 |
| Other ingredients | |
| Titanium dioxide | 0.5 |
| Buffer (pH 5.5) | 2.5 |
| Preservative, perfume, antioxidant | 2.5 |
| Emollient | 5 |
| Water | 22.7 |
| | 100 |

The emulsion will be stable at storage temperatures up to 42° C. for several months. It will also be stable to freeze-thaw cycling.

The emulsion can be used in the topical treatment of acne.

EXAMPLE 9

An anti-acne cream can be prepared from the following ingredients:

|  | % |
|---|---|
| Silicone oil ingredient | |
| Silicone Q2-3225C | 28 |
| Emulsifier | |
| Sorbitan sequioleate | 2 |
| Alkyl lactate | |
| Ethyl lactate | 12 |
| Alkanol | |
| Ethanol | 25 |
| Electrolyte | |
| Zinc sulphate (ZnSO$_4$.7H$_2$O) | 0.3 |
| Other ingredients | |
| Titanium dioxide | 0.5 |
| Buffer (pH 5.5) | 2.5 |
| Preservative, perfume, antioxidant | 2.5 |
| Emollient | 7.2 |
| Water | 20 |
|  | 100 |

The emulsion will be stable at storage temperatures up to 42° C. for several months. It will also be stable to freeze-thaw cycling.

The emulsion can be used in the topical treatment of acne.

EXAMPLE 10

An anti-acne cream can be prepared from the following ingredients:

|  | % |
|---|---|
| Silicone oil ingredient | |
| Silicone Q2-3225C | 32 |
| Emulsifier | |
| Sorbitan trioleate | 2.5 |
| Alkyl lactate | |
| tert-Butyl lactate | 10 |
| Alkanol | |
| Ethanol | 10 |
| iso-Propanol | 12 |
| Electrolyte | |
| Zinc sulphate (ZnSO$_4$.7H$_2$O) | 0.3 |
| Other ingredients | |
| Titanium dioxide | 0.5 |
| Buffer (pH 5.5) | 2.5 |
| Preservative, perfume, antioxidant | 2.5 |
| Emollient | 6.5 |
| Water | 21.2 |
|  | 100 |

The emulsion will be stable at storage temperatures up to 42° C. for up to four months. It will also be stable to freeze-thaw cycling.

The emulsion can be used in the topical treatment of acne.

EXAMPLE 11

An anti-acne cream can be prepared from the following ingredients:

|  | % |
|---|---|
| Silicone oil ingredient | |
| Silicone Q2-3225C | 29 |
| Emulsifier | |
| Polyglycol sesquioleate | 2 |
| Alkyl lactate | |
| iso-Propyl lactate | 11.5 |
| Alkanol | |
| iso-Propanol | 21 |
| Electrolyte | |
| Zinc sulphate (ZnSO$_4$.7H$_2$O) | 0.3 |
| Hydrophobic agent | |
| R812 | |
| Other ingredients | |
| Titanium dioxide | 0.5 |
| Buffer (pH 5.5) | 2.5 |
| Preservative, perfume, antioxidant | 2.5 |
| Emollient | 7 |
| Water | 23.7 |
|  | 100 |

The emulsion will be stable at storage temperatures up to 42° C. for several months. It was also stable to freeze-thaw cycling.

The emulsion can be used in the topical treatment of acne.

I claim:

1. A water-in-oil emulsion suitable for topical application to human skin for the treatment of acne, which comprises in addition to water:
   (i) from 2 to 30% by weight of a C$_1$ to C$_4$ alkyl lactate, or a mixture thereof;
   (ii) from 15 to 50% by weight of a silicone oil ingredient comprising a dispersion in a volatile siloxane of a polymer of dimethyl polysiloxane with polyoxyethylene and/or polyoxypropylene side chains having a molecular weight of from 10,000 to 50,000, and having the structure:

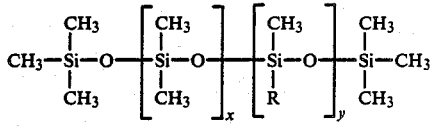

where R is

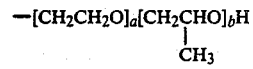

a has a value of from 9 to 115,
   b has a value of from 0 to 50,
   x has a value of from 133 to 673, and
   y has a value of from 25 to 0.25;
   (iii) from 0.5 to 10% by weight of a nonionic liquid emulsifier having an HLB value of from 1 to 7;
   (iv) from 5 to 40% by weight of a C$_1$ to C$_4$ alkanol, or a mixture thereof; and
   (v) from 2 to 10% by weight of a hydrophobic silica having an organic moiety;
   the emulsion consisting essentially of an aqueous phase forming from 10 to 98% by volume and an oily phase forming from 2 to 90% by volume.

2. The emulsion according to claim 1, wherein the alkyl lactate is chosen from methyl lactate, ethyl lactate, n-propyl lactate, iso-propyl lactate, n-butyl lactate, iso-butyl lactate, tert-butyl lactate and mixtures thereof.

3. The emulsion according to claim 1, wherein the polymer of dimethyl polysiloxane with polyoxyethylene and/or polyoxypropylene side chains is chosen from those polymers where:
   a has a value of from 10 to 114,
   b has a value of from 0 to 49,
   x has a value of from 388 to 402, and
   y has a value of from 15 to 0.75;
the group R having a molecular weight of from 1000 to 5000.

4. The emulsion according to claim 1, wherein the polymer of dimethyl polysiloxane with polyoxyethylene and/or polyoxypropylene side chains is a polymer where:
   a has the value 14
   b has the value 13
   x has the value 249
   y has the value 1.25.

5. The emulsion according to claim 1, wherein the volatile siloxane is a polydimethyl cyclosiloxane.

6. The emulsion according to claim 1, wherein the silicone oil ingredient comprises from 1 to 20% by volume of the polymer and from 80 to 99% by volume of the volatile siloxane.

7. The emulsion according to claim 1, which comprises:
   (i) from 5 to 20% by weight of ethyl lactate;
   (ii) from 15 to 40% by weight of a 10% by volume dispersion in tetradimethyl cyclosiloxane of a polymer of dimethyl polysiloxane with polyoxyethylene and/or polyoxypropylene side chains having the structure:

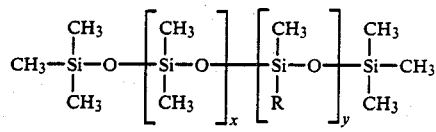

where R is

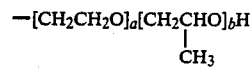

(iii) from 1 to 5% by weight of a nonionic liquid emulsifier having an HLB value of from 1 to 7;
   (iv) from 10 to 30% by weight of an alkanol chosen from ethanol and iso-propanol or mixtures thereof; and
   (v) from 0.1 to 10% by weight of an inorganic salt;
the aqueous phase forming from 50 to 90% by volume and the oily phase forming from 10 to 50% by volume of the emulsion.

8. The emulsion according to claim 1, which is a cream.

* * * * *